United States Patent [19]

Hill et al.

[11] 4,362,815

[45] Dec. 7, 1982

[54] PROCESS FOR THE PREPARATION OF DEFECTIVE MUTANTS OF MICROORGANISMS

[75] Inventors: Frank F. Hill, Mettmann-Obschwarzbach; Joachim Schindler, Hilden; Rolf Schmid, Dusseldorf; Wolfgang Preuss, Monheim; Alfred Struve, Hilden, all of Fed. Rep. of Germany

[73] Assignee: Henkel Kommanditgesellschaft auf Aktien, Dusseldorf, Fed. Rep. of Germany

[21] Appl. No.: 128,223

[22] Filed: Mar. 7, 1980

Related U.S. Application Data

[63] Continuation-in-part of Ser. No. 29,415, Apr. 12, 1979, Pat. No. 4,320,195.

[30] Foreign Application Priority Data

Mar. 7, 1979 [AT]  Austria ................................. 1709/79

[51] Int. Cl.$^3$ ...................... C12N 15/00; C12N 1/20; C12P 33/16
[52] U.S. Cl. .................................... 435/172; 435/253; 435/55
[58] Field of Search .................. 435/55, 136, 253, 172

[56] References Cited

U.S. PATENT DOCUMENTS 3,759,791  9/1973  Marshecki et al. ................... 435/55
4,029,549  6/1977  Antosz et al. ......................... 435/55
4,032,408  6/1977  Jin et al. ................................ 435/55
4,062,729  12/1977  Biggs et al. ......................... 435/136

OTHER PUBLICATIONS

Lamanna et al., Basic Bacteriology, Its Biological and Chemical Background, 3rd Ed., The Williams & Wilkins Co., pp. 723–727, (1965).

Metzler, Biochemistry, The Chemical Reactions of Living Cells, Academic Press Inc., pp. 945 and 946, (1977).

Whitmarsh, The Biochemical Journal, vol. 90, pp. 23p and 24p, (1964).

Martin et al., European J. Appl. Microbial, vol. 2, pp. 243–255, (1976).

*Primary Examiner*—Alvin E. Tanenholtz
*Attorney, Agent, or Firm*—Forrest L. Collins

[57] ABSTRACT

For the production of 17-C-steroid-α-propionic acid compounds by microbial side chain degradation on 17-C-side chain steroid substrates wild strain microorganisms selected in predetermined manner are subjected to a multi-stage mutation and selection. The resultant mutant strains are capable of supplying the desired compounds, e.g. Δ-4 BNC and/or Δ-1,4 BNC in high yields even in the absence of inhibitors arresting the growth and/or degradation of the steroid ring. Wild strains and mutants particularly suitable, and their choice, production and use, are described.

12 Claims, No Drawings

PROCESS FOR THE PREPARATION OF DEFECTIVE MUTANTS OF MICROORGANISMS

This application is continuation-in-part of U.S. patent allowed application Ser. No. 029,415 filed Apr. 12, 1979 now U.S. Pat. No. 4,320,195.

The subject of this application is inter alia a process for the production of block mutant microorganisms which are capable of effecting the technical production of 17-C-steroid-α-propionic acid compounds, in particular for producing 3-oxo-pregna-4-ene-20-carboxylic acid (Δ-4 BNC) and/or 3-oxo-pregna-1,4-diene-20-carboxylic acid (Δ-1,4 BNC) from 17-C-side chain steroid substrates, e.g. from sterol compounds of animal or vegetable origin, by at least thorough selective side chain degradation also in the absence of inhibitors preventing steroid ring degradation and/or growth under aerobic conditions. The process is characterised by the fact that 1. a wild strain microorganism is isolated and cultured which is capable of growing on sterol compounds as the sole source of carbon, preference being given to 17-C-side chain degradation over ring degradation.
2. the wild strain is subjected to a mutation treatment known per se,
3. The mutant population is cultivated on a separation medium on which the mutants supplying the 17-C-steroid-α-propionic acid compounds do not appreciably grow, whilst undesired accompanying mutant strains grow and are thereby killed off or die during their growth, and
4. the remaining residue of the mutant strains are cultivated on the 17-C-side chain sterols and the strains with optimum production of 17-C-steroid-α-propionic acid compounds are isolated.

Δ-4 BNC and Δ-1,4 BNC are valuable intermediate products in the production of steroid compounds of the progesterone series: Structural formulae are as follows:

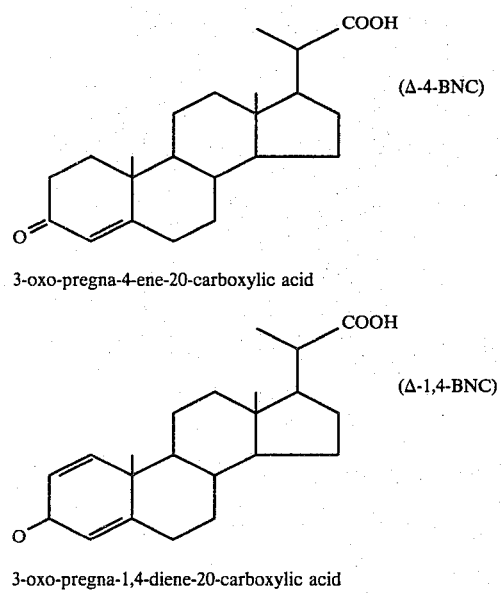

3-oxo-pregna-4-ene-20-carboxylic acid (Δ-4-BNC)

3-oxo-pregna-1,4-diene-20-carboxylic acid (Δ-1,4-BNC)

In the first step of the process, wild strains are preferably chosen and cultivation under aerobatic conditions, which when grown on sterol compounds, with saturated or unsaturated alkyl groups 17-C- with 8 to 10 carbon atoms produce a selective degradation effect—measured under standard conditions according to the formula $$I = a \cdot 10^b$$

where a is the growth factor and b the selectivity index of the wild strain and the value of the selectivity index is at least 10, preferably at least 100, and in particular at least $10^5$. It is particularly preferred to select and introduce in the following mutation wild strains whereof the selectivity factor b is at least 1, advantageously at least 2, and the growth factor a of which is similarly at least 1; it may also be preferable to consider the wild strains first according to their selectivity factor b—with mostly higher values for b—and only when according to their growth factor a.

The determination of this selectivity factor b is effected by aerobic culture of the wild strains in parallel testing on radioactively tagged sterol compounds, e.g. 4-14 C- and 26-14 C-Cholesterol or the corresponding radioactively tagged sitsterol compounds. The so-called Warburg vessel is advantageously used for this. The radioactive $CO_2$ evolved during the substrate cleavage is collected in a base and measured in the scintillation counter. The relativity factor b is given as the dimensionless ratio of the radioactivity thus measured.

$$b = \frac{^{14}CO_2\text{-sterol compound from the (26-}^{14}C\text{)-sterol compound}}{^{14}CO_2 \text{ from the ring system (14-}^{14}C\text{)-sterol compound}}$$

This selection of the wild strain according to its selectivity factor b requires very tedious working with two radioactively tagged sterol compounds in parallel tests.

The subject is furthermore a process for the preparation of 17-C-steroid-α-propionic acid compounds, especially Δ-4 BNC and/or Δ-1,4 BNC, by microbial side chain degradation on 17-C-side chain steroid substrates under aerobic conditions, which is characterised by the fact that if desired even in the absence of inhibitors for the steroid ring degradation and/or the growth inhibitors use is made of defective block mutants as microorganisms which have been obtained according to the previously depicted production process. Finally, the Main Patent concerns suitable wild strains and the new defective block mutant strains obtained therefrom according to the process described.

The subject of the present invention is beyond this a further development of these various aspects of the teaching of the parent application. It has been found surprisingly that as wild strain microorganisms for the mutation, separation and final culture of the mutant population and lastly therewith for the process for the preparation of 17-C-steroid-α-propionic acid compounds from 17-C-side chain steroid substrates such wild strain microorganisms are especially suitable which on growing on sterol compounds of the kind referred to in the presence of inhibitors for the enzymatic ring degradation of the sterol compounds yield at least partially 17-C-steroid-α-propionic acid compounds.

The present development is distinguished from the process described at the start of the parent application for the preparation of the desired microorganic defective mutants in Stage 1, i.e. in the step of choosing the actual wild strain microorganisms. Whereas according to the teaching of the parent application suitable strains of microorganisms are identified by the fact that their enzyme activity on the one hand for the side band degradation and on the other hand for the ring degradation are definite and comparable with one another, as criterium for the suitability of the wild strain according to the present further development, the capability of the wild strain to supply sterol compounds with definite side chain substitution in 17-C- in the presence of inhibitors for the degradation of the sterol ring is fundamental.

Inhibitors for the enzymatic ring degradation with culture of microorganisms on sterol compounds are fully described in technical literature, compare for instance Ch. K. A. Martin "Microbial Cleavage of Sterol Side Chains". Adv. Appl. Microbiol. 22, 29–58 (1977), especially the sub-heading IV, B, pages 44–50 etc., as well as Nagasawa et al: Agr. Biol. Chem. 34, 838–844 (1970).

That known wild strain microorganisms in the presence of such inhibitors can occasionally be in a position to form Δ-1,4 BNC out of natural animal or vegetable sterol compounds such as cholesterol or sitosterol has been briefly reported, see K. Arima et al, "Microbial Production of 3-Oxobisnorchola-1,4-dien-22-oic Acid" in Agric. Biol. Chem. 42 (2) 411–416 (1978). The process according to the invention employs such wild strain microorganisms as starting material for obtaining better and more effective defective mutants. Preferably, definitely selected wild strains of this kind are used as a basis for the recovery of the defective mutants according to the invention.

The modification according to the invention of the process or processes of the parent application for the identification of wild strain microorganisms suitable for the subsequent mutation treatment rests on two determinations: In the search for microorganisms which consume sterol compounds of the known type, strains which supply the sterol compounds 17-C-steroid-α-propionic acid compounds and especially Δ-4 BNC and/or Δ-1,4 BNC in the presence of inhibitors for the enzymatic ring degradation can be isolated with a surprisingly high quota of success. In fact such strains are also already described and established by deposit. It may be further established that wild strains of this kind are especially suitable as starting material for the subsequent mutation and selection in the sense of the teaching of the parent application, in order thereby to supply finally defective mutants suitable for gaining the 17-C-steroid-α-propionic acid compounds by microbial side chain degradation on 17-C-side chain steroid substrates in a technical treatment and in good yield. Defective mutants of the kind according to the invention are also particularly suitable for the inhibitor-free production of Δ-4 BNC and/or Δ-1,4 BNC.

Such wild strains of known type which upon growth on sterol compounds with saturated or unsaturated alkyl groups in 17-C-position, preferably with 8 to 10 C-atoms under standard conditions yield 17-C-steroid-α-propionic acid compounds of at least 5% by weight, preferably at least 10% by weight referred to the sterol compound(s) in the standard test have proved to be especially suitable. The conditions of this standard test are described below in connection with the determination of the selectivity factor p.

The preferred wild strains investigated in the selection stage according to the invention form upon their growth on sterols as a single supplier of carbon in a usual culture medium with the addition of inhibitors for the enzymatic ring degradation on the sterol as a rule Δ-4 BNC and/or Δ-1,4 BNC. The selection of the microorganism within the ambit of the present invention can accordingly be adjusted in a preferred embodiment to the formation capability of the wild strain microorganism—i.e. yield of Δ-4 BNC and/or Δ-1,4 BNC under standard conditions. The determination of this capability and therewith the selectivity factor p of the wild strain culture is effected, therefore, under the following standard conditions:

Yield or selectivity factor p of the wild strain

The microorganism strain is incubated at 30° C. in the shaking machine (shaking frequency: 150 cycles per min) in a 500 ml Erlenmeyer flask (100 ml culture solution of the composition described below). This and all further steps of the microorganism culture is carried out under aerobic conditions.

The culture medium has the following composition (percentage weight in each case):

0.20% $K_2HPO_4$
0.05% $NaH_2PO_4$
0.80% peptone
0.90% yeast extract
0.30% glucose
$p_H$ 7.2

After 48 hours culture time at 30° C. an addition of 0.1% Tween 80 (Polyoxyethylene sorbitane mono-oleate) and 0.1% 17-C-side chain sterol compound, e.g. cholesterol or sitosterol follows. After a further 4 hours there follows the addition of the inhibitor in a concentration of $10^{-3}$ Mol/l (M).

At the time of the addition of the inhibitor the $p_H$ value of the medium is adjusted to 8.0. After further incubation for 62 hours, the culture is harvested and the content of Δ-4 BNC and/or Δ-1,4 BNC determined by customary methods as a percentage weight relatively to the sterol compound added.

The selectivity factor p is calculated from the percentage BNC yield thus:

p = % BNC Yield/10

Within the group of the microorganic strains formed in the presence of BNC inhibitors, as a rule the strains are the more suitable for the invention the higher the BNC yield and therewith the greater selectivity factor p in each case. As the lower limit for suitable wild strains at least 0.5 is to be regarded in general, strains with a relativity factor at least 1 or 1.5 being given preference. Strains with a relativity factor of 2 or more have proved especially suitable, whereas according to the best known results, selectivity factors of the order of 4 have been reported.

As inhibitors for inhibiting the enzymatic degradation of the sterol ring system from the known group of compounds for this, for example, α,α'-dipyridyl, o-phenanthroline, 8-oxochinoline and quite general media which form complex salts with heavy metals under chelat formation, such as 1-nitroso-2-naphthol, salicylaldoxime, nitroso-phenylhydroxylamine, 1-nitroso-2-naphthal-3,6-disulfonic acid, tetrahydroxyanthraguinone, and the like are suitable. Preferred inhibitors for carrying out the standard test for determination of the selectivity factor p are α,α'-dipyridyl and o-phenanthroline, it being sufficient for the determination of the yield according to the standard test if the smallest yield required with one of these two inhibitors is produced under otherwise similar growth conditions.

Independently of the determination of the selectivity factor p the preferred choice of suitable wild strains in the ambit of the invention is effected under additional separate determination of the rate of growth of the particular wild strain. The information given in the parent application for ascertaining the corresponding growth factor a applies to this.

Growth factor "a"

The microorganism strain in question is incubated in a 500 ml Erlenmeyer flask (100 ml culture solution of the composition described below) at 30° C. under aerobic conditions on a shaking machine (shaking cycles: 150 per min).

The culture medium has the following composition (per liter):

| | |
|---|---|
| 1.0 g | $KH_2PO_4$ |
| 0.5 g | $MgSO_4.7\ H_2O$ |
| 0.1 g | NaCl |
| 0.1 g | $CaCl_2.2\ H_2O$ |
| 5 g | $(NH_4)_2SO_4$ |
| 1.0 g | Tween 80 (Polyoxyethylene sorbitane monooleate) |
| 2.0 g | 17-C-side chain sterol compound, e.g. cholesterol or sitosterol |
| 0.5 g | yeast extract |
| 0.1 g | l-histidine |
| 0.02 g | dl-methionine |
| 0.02 g | dl-tryptophane |
| 2 γ | biotine |
| 400 γ | calcium pantothenate |
| 2 γ | folic acid |
| 2000 γ | inosol |
| 400 γ | niacin |
| 200 γ | p-aminobenzoic acid |
| 400 γ | pyridoxyine hydrochloride |
| 200 γ | riboflavin |
| 400 γ | thiamine hydrochloride |
| trace elements in solution | |
| pH value of the culture medium 6.8. | |

For measuring the growth (cell density) adequate quantities of cell suspension are taken out periodically from the agitated cultures, and the particular extinction (E') is measured against distilled water in a Zeiss photometer (Type PL 4) at a wave length of 620 nm (layer thickness d=1 cm). The initial extinction $E_0$ before the beginning of growth at time $t_0$ is about 0.775. The suspensions are so far diluted that measurements can be in the region of E'=0.7.

The growth factor a results as the maximum optical density of the cell suspension at the end of the logarithmic growth phase (Time $t_1$, extinction $E_1$) which is reached after 5 days at the latest, under the given culture conditions, i.e. $a = \Delta E = E_1 - E_0$.

According to the invention such microorganic wild strains are especially suitable for the following mutation and selection, which having regard to the factors a and p described above, provide a selective degradation performance according to the general formula $$I = a \cdot 10^p$$

(I=selectivity index) with a numerical value of at least 1, preferably 2 and in particular at least 20. Still higher values could come into consideration, e.g. values of $I \geqq 1.10^3$ or even $\geqq 5.10^3$. In the frame of the invention, wild strains with growth factors a of at least 0.2, preferably at least 2 and especially 4 or more are particularly preferred.

Also within the scope of the present development for the choice of wild strains best suitable for the further steps of the process according to the invention, it can be advantageous to balance the factors a and p against one another, to give preference to wild strains with a particularly high selectivity factor p and, when there is a choice between different isolated wild strains, to choose first the one with the highest value for this selectivity factor p. Conversely a particularly good growth—expressed by a specially high value for the growth factor a can naturally also give such a wild strain the preference for the subsequent mutation and the selection of the mutant population which follows.

In the presence of inhibitors Δ-4 BNC and/or Δ-1,4 BNC the wild strains provided find greater latitude in the microorganic classification. Such strains for example, as Achromobacter, Arthrobacter, Bacillus, Brevibacterium, Corynebacterium, Flavobacterium, Microbacterium, Mycobacterium, Nocardia, Protaminobacterium, Serratia or Streptomyces, are suitable. As stated the literature also already gives reference to strains which on being cultured on 17-C-side chain sterols in the presence of inhibitors such as α,α'-dipyridyl and o-phenanthroline Δ-1,4 BNC supply various yields, c.f. K. Arima et al and elsewhere.

After the choice of the suitable wild strain has been made, then the further mutation and selection process in the sense of the disclosure of the Main Patent can follow. The following applies in detail for this:

Mutation treatment (Stage 2)

The mutation of the selected wild strain is effected in the following manner. It can, for example, be effected by high energy radiation with ultraviolet or X-rays. However, the treatment of the cells with mutagenic agents is also particularly suitable. Suitable mutagenic agents are, for example, nitrosoguanidine compounds such as 1-methyl-3-nitro-1-nitrosoguanidine or ethylmethane sulfonate. In detail reference hereto can be made to the general disclosure of the status of the technology, see for example U.S. Pat. No. 4,029,549, column 2, line 57 et seq with the references contained therein.

Basically, it is also true for this invention, that the result of the mutation of the wild strain is uncertain insofar as the characteristics of the defective mutants obtained are not predictable in detail. Nevertheless, principles for an optimum release of mutation may be laid down, as the laws of statistics can be applied to a population of microorganisms. From the literature processes are known for determining the optimum conditions for the induction of mutation (see E. A. Adelberg, M. Mandel, GCC Chen (1965) "Optimal Conditions for Mutagenisis by N-methyl-N'-nitro-N-nitrosoguanidine in *Escherichia coli*" Biochem. Biophys. Res. Commun. 18, 788–795).

In general, to increase the abundance of mutations in the microorganism population the concentration and time of action of mutagenic agents will be so chosen that a part of the microorganism population is already lethally damaged. In this way the abundance of the various mutations in the surviving part of the population is more or less strongly increased.

Within the framework of the process according to the invention the conditions of concentration and time of action of the mutagenic agent are so chosen that the starting population is rendered inactive by the treatment to 10–99.999%. Preferably a killing rate of 90–99.99% is chosen.

The process stage 2 of mutation is followed by process stages 3 and 4 of the parent application.

Stage 3

For the succeeding selection of the specific mutants desired according to the invention out of the large population of the microorganisms after the mutation treatment, culture conditions according to the invention are chosen, under which the altered specific characteristics of the mutant strains produced become of advantage in the selection. The enrichment of the desired defective mutants is effected according to the invention often under conditions such that the specific mutant does not grow or substantially does not grow, while undesirable accompanying organisms grow and are killed off by or during their growth. In this manner, those block mutant strains are sucessfully isolated whose ring-degrading enzymes are blocked, but which now as before are capable of degrading the 17-C side chain on the sterol compound, it being ensured by further measures, especially in this stage 3, that just such block mutants can be isolated which form preferentially the α-propionic acid group in 17-C position during side chain degradation.

For this purpose, the mutant population is cultivated in process stage 3 on a separation medium which finally serves as the enrichment medium for the desired mutant strains. An aqueous nutrient medium may be used as mutant separation medium, which contains as carbon source a steroid compound with a 17-C side chain with only a limited number of carbon atoms or also no side chain in the 17-C position. Besides the steroid compounds which are not substituted in 17-C position, those which contain side chains with up to five carbon atoms are suitable as carbon source in this mutant separation medium.

It is preferable, however, to use a steroid compound with three carbon atoms in the 17-C side chain as carbon source in this mutant separation or enrichment medium, it being desirable to use a 17-C-steroid-α-propionic acid compound or a plurality of such desired 17-C-steroid-α-propionic acid compounds as the sole carbon source.

It may be further preferred to use as carbon source in this mutant separation medium those 17-C-steroid-α-proprionic acid compounds the production of which is ultimately desired by means of the block mutants cultivated according to the invention. Thus if Δ4 BNC or Δ1,4 BNC is finally to be recovered as the process product from sterols of vegetable or animal origin according to the invention, it may be desirable to use Δ4 BNC and/or Δ1,4 BNC as the sole carbon source in the mutant separation or enrichment medium of this stage 3.

In other respects, the process is operated with conventional nutrient solutions under aerobic conditions.

The mutated microorganisms which, due to the mutation treatment, have lost their ability to grow on the carbon sources now available, are not able to reproduce themselves when the mutant separation medium is incubated, i.e. they do not grow. Another portion of the mutant population which either has not been damaged sufficiently in the mutation treatment of stage 2 or has suffered other defects is capable of growing on the carbon source of the mutant separation medium, i.e. reproduction occurs during incubation.

The invention makes use of this differing behaviour in choosing the conditions in the mutant separation medium so that the growing strains are killed off because of or during their growth while the non-growing mutant strains are not damaged.

Such a separation is possible, for example, by the addition of antibiotics, e.g. by the addition of penicillin compounds. The addition of penicillin compounds leads to the killing-off of the fraction of the growing strains of microorganisms while the non-growing strains remain unharmed.

The defective mutant strains aimed at according to the invention may then be isolated from the remaining undamaged block mutants by means of the known Lederberg stamp method. As regards the procedure used here, the penicillin enrichment method and the Lederberg stamp method, reference is made, for example, to J. Amer. Chem. Soc. 70, 4267, (1948) Davis, B. D. (Penicillin enrichment method), J. Bact. 63, 399 (1952) Lederberg, J. Lederberg, E. M. (Lederberg stamp method).

Another appropriate method according to the invention is the extermination of unsuitable mutants by the use of culture media which contain radioactive components which eventually damage the growing cells especially under incorporation in the cell structure. Here it is appropriate, for example, to kill off the unsuitable mutants by a culture medium which contains $^{32}P$ especially in the form of the salt $NaH_2{}^{32}PO_4$. In regard to this inactivating technique see Fuerst, C. R., Stent, G. S.: Inactivation of Bacteria by Decay of Incorporated Radioactive Phosphorus, J. Gen. Physiol. 40, 73–90 (1956).

Stage 4

The defective block mutants thus isolated and selected may now be cultivated on a common culture medium and then, if desired, subjected to a further selection. This selection may be effected, for example, according to the result desired for the microorganism strains on the intended starting material, for example, on natural or vegetable sterol compounds, in which case particularly the chemical nature of the products of metabolism of the growth of the microorganisms and the growth enthusiasm of the strains may be decisive. Naturally, block mutants, having optimum productivity of the ultimately desired process product will be preferred. These strains may then be used in the commercial-scale process. Cultivation and selection may be repeated here once or several times.

Within the framework of the process according to the invention, it is however also possible to repeat once or several times the sequence of the process stages the mutation according to stage 2, and the succeeding mutant separation according to stage 3 if a still stronger effect of the mutagenic agents on the defective mutant strains appears desirable for achieving ultimately optimal production results. Finally, processing is then effected generally according to stage 4.

According to the invention it can be preferable to investigate the specially desired defective mutant strains by their transformation performance in a standard test. The ability of the strain to produce is determined with reference to the formation of Δ-4-and/or Δ-1,4 BNC. For the determination of the yield according to this standard test the following conditions apply:

BNC yield according to a standard test

The defective mutant strain to be examined is cultivated in the 500 ml Erlenmeyer flask with 100 ml of nutrient solution having the following composition:

0.8% of peptone, 0.9% of yeast extract, 0.3% of glucose, 0.06% of Tween 80 (polyoxyethylene sorbitane monooleate), 0.06% of cholesterol or sitosterol, pH 7.2. The strain is precultivated on the shaking machine (shaking frequency 150 rpm) at 30° C. for 62 hours. After having added 0.1% of BRIJ 35 (polyoxyethylene monolauryl ether) and 0.1% of the sterol compound, incubation is continued for 120 hours. After termination of the incubation, samples are taken and then extracted and analysed by thin layer chromatography. The percentage yield in Δ-4- and/or Δ-1,4 BNC is determined. All percentages are percentages by weight. The yield is referred to the quantity by weight of the sterol compound to be transformed introduced in the standard test.

The defective mutant strains preferred in accordance with the invention yield under these standard conditions with cholesterol or sitosterol as steroid substrates, a minimum of 15% by weight, preferably 30% by weight and more. With the use of cholesterol as steroid substrate the minimum favourable yield in accordance with this standard test can amount to 50% by weight or more, specially effective strains giving BNC yields in the region of 70 to 80% by weight. With the use of sitosterol as steroid substrate the yield may be somewhat lower, but even here may reach values in the region of 40 to 50% by weight.

Also the present invention contemplates furthermore the process of producing 17-C-steroid-α-propionic acid compounds and particularly the production of 3-oxo-pregna-4-ene-20-carboxylic acid and/or 3-oxo-pregna-1,4-diene-20-carboxylic acid by means of the defective block mutants obtained from steroid compounds with side chains in 17-C position, particularly of animal or vegetable origin.

Beside or in place of the use of steroid substrates of natural origin, such as cholesterol, sitosterol and so forth, compounds derived therefrom such as cholestenone, sitostenone, stigmastenone and the like may be used as starting material.

The selective transformation of the steroid substrate selected as starting material, i.e. for example of a natural sterol compound, may be effected in a manner known per se after having provided and selected the defective mutants according to the previously described procedure. Thus, for example, the steroid compound selected as starting material may be added to the culture during the incubation period or it may be introduced into the culture medium before the inoculation of the block mutants. One steroid compound or a mixture of a plurality of steroid compounds may be used. The steroid compounds to be selectively degraded are preferably used in the culture in amounts of about 0.1 to 100 g/l. The optimum concentration of the sterol compound to be transformed in the cultivation stage is generally dependent on the strain and may be determined in each case by simple preliminary tests. In general, the concentration of the sterol compound in the medium preferably does not exceed 20 g/liter and, in many cases, 15 g/liter, but amounts of more than 1 g/liter are preferred.

The culture is cultivated in a growth medium which, as carbon source, contains either the sterols to be transformed or also additional metabolizable carbon sources as well as the nutritive and growth materials usually needed by these microorganisms. Particularly favourable for the growth of the organisms are for example paraffin, glycerol, carboxylic acids, starch, dextrin, saccharose, sucrose, glucose, fructose and sugar-containing waste materials. Suitable nitrogen sources include ammonium salts, nitrates, peptone, corn steep liquor, soya meal, distiller's wash and fish meal. Moreover, fermentation accelerators such as yeast extract and vitamins may be added. The nutrient medium additionally contains advantageously inorganic salts such as sodium potassium or ammonium phosphates as well as calcium, magnesium, manganese or iron salts.

It may therefore be preferred for the substrate to be subjected to side chain degradation not to be added to the reaction medium in a single operation, but to be added gradually during the course of the reaction. Advantageously in this embodiment the substrate starter is added continuously to the reaction mixture in the course of the degradation reaction. In this way the yield of the desired degradation product is increased.

The emulsification of the sterols in the culture medium is preferably effected by means of known emulsifiers, e.g. by means of fatty acid, sorbitane esters or their ethylene oxide addition products, polyoxyethylene monolauryl ether or fatty acid amino-alkylbetain.

The culture medium used is preferably sterilized by heating before the beginning of the cultivation of the bacteria. After cooling and inoculation with a suitable seed culture of the transforming bacteria strain, the culture medium is incubated between 25° and 55°, preferably at 27°–30° C. The pH of the culture medium ranges between 4 and 8.5, preferably in the range of 7.0–8.0. The culture is supplied with oxygen by shaking, stirring or injection of gas, and incubated until the sterol is degraded to the desired degree. As a rule, the degradation of the sterol requires from 24 to 160 hours depending on the concentration of the substrate and on the fermentation conditions.

The process product obtained this way and usually accumulated in the fermentation broth may then be recovered from the reaction mixture in a manner known per se. Thus, for example, BNC compounds may be isolated from the culture medium, before or after the separation of the cells, by extraction within organic solvents such as methylisobutylketone, acetic acid ester, n-hexanol, n-octanol, chloroform or n-hexane.

For instance an isolation of BNC compounds is achieved by extracting one liter of a fermentation broth containing 1 g BNC with about the same volumes of organic solvents such as methylisobutylketone, acetic acid ester, n-hexanol, n-octanol, chloroform, or n-hexane in the perforator, homogenizer, or separating funnel. In the latter two cases, a centrifugation step must be added for the separation of the BNC containing organic phase from the emulsion.

After evaporating the solvent, a BNC-containing residue is left which after recrystallisation, e.g. from benzene, may be processed to pure BNC having a melting point of 233°–236° C.

The solvent extraction is possible, above all, in the acidic pH range. To this end, for example, the sample is adjusted to about pH 2 with 50% $H_2SO_4$ and extracted with methylisobutylketone, acetic acid ester, n-hexanol, n-octanol, chloroform, or n-hexane in the manner described above. After evaporation of the organic phase, a residue containing BNC is obtained, which again after recrystallisation, leads to a pure product having a melting point of 233°–236° C. The extraction may also be performed in the neutral range.

Alternatively, a purification by anion exchange is also possible. To this end, the fermentation broth is first desirably concentrated and then adjusted to an alkaline pH, e.g. 12. After adding a limited amount of methanol and agitating in the homogenizer, the cell mass is separated by means of a basket centrifuge. The supernatant alcohol-water is pumped over an ion-exchange column which is filled with an anion exchanger resin, e.g. in acetate form. The BNC formed is thereby completely bound to the ion-exchanger. Elution with 10 acetic acid in methanol gives a product which chiefly contains BNC. After recrystallisation, pure BNC with a melting point of 233°–236° is obtained.

According to a preferred embodiment, the isolation of BNC-compounds from the fermentation liquid is simply realised by precipitation in the acidic range and filtration. To this end, and fermentation liquid adjusted to be alkaline is first filtrated to permit the removal of cell material and of other solid components. Thereafter, one acidifies, and the BNC precipitates in a solid form which can be filtered and may be recovered for instance by simple filtration under suction.

For the acidification, any mineral acid may be used, but also organic acids, e.g. acetic acid, and even gaseous $CO_2$. With the pH 5, the complete precipitation is practically achieved. It may be favourable for a better filtration possible, to shortly heat the suspension.

The isolated solid may contain up to 90% of BNC-compounds. The pure compounds may be recovered by recrystallisation.

Special details of the invention

By means of the wild strain selection methods according to the invention a large number of wild strains can be isolated in a relatively short time which are basically suitable as starting material for the mutation process according to the invention. The most important of these wild strains have been deposited under the following Deposit Numbers: ATCC 31455, ATCC 31458, DSM 1418, DSM 1419, DSM 1423, DSM 1424, DSM 1425, DSM 1426, DSM 1427, DSM 1428, DSM 1429, DSM 1430, DSM 1431, DSM 1432.

A special strain of bacteria is concerned with these microorganisms, which may be partially attributed to the coryneform bacteria. The extract identification will follow in time.

As a matter of interest it may be established that the wild strain Chol. 73 which is deposited under number CBS 660.77 at Baarn, Netherlands, as well as under number ATCC 31384 at Rockville, Md., U.S.A., fulfils the selection method according to the invention, i.e. in the presence of inhibitors yields substantial quantities of Δ-4 and/or Δ-1,4 BNC compounds. Also the wild strain 50 which belongs to the group of coryneform bacteria is therefore in principle also a suitable starting material for the subsequent mutation into the desired defective mutants.

From the wild strain ATCC 31455 above-mentioned, defective mutants are obtained by the mutation treatment according to the invention which are highly effective in the sense of the teaching of the invention and for example make possible an inhibitor-free highly technical production of Δ-4 and/or Δ-1,4 BNC compounds from cholesterol or sitosterol. This also applies to defective mutant strains of other wild strains mentioned, for example, the wild strain ATCC 31458. Defective mutant wild strains deposited under number ATCC 31456 and ATCC 31457—derived from wild strain ATCC 31455—are especially effective. The defective mutants ATCC 31459 and ATCC 31460 were developed on the basis of wild strain ATCC 31458 and deposited.

All the wild and defective mutant strains mentioned here fall within the framework of the invention insofar as they are not already the subject of the Main Patent.

EXAMPLE 1

A. Recovery of suitable wild strains

According to the customary enrichment methods, sterol degenerated microorganisms are isolated from soil samples, which are first tested in a plate test for their capability of growing on β-sitosterol. Strains showing a clear colony growth are taken as pure cultures and subjected to further selection procedures.

B. Determination of the growth factor a

For ascertaining the growth factor a the isolated pure culture is cultivated under the aerobic conditions given in the general description. To determine the optical density of the cell suspension respective samples are taken at 24-hour intervals and the measurement carried out according to the information on the standard test in the descriptive part. The investigation is stopped when the actual cell maximum density is obtained.

C. Determination of the selection factor p

The wild strains showing the best growth in the shaking flask test with β-sitosterol are subsequently tested in the inhibitor test as to their capacity for intermediate BNC aggregation. The aerobic culture of the strains takes place for this purpose in 100 ml culture solution of the following composition: 0.20% $K_2HPO_4$, 0.05% $NaH_2PO_4$, 0.80% peptone, 0.90% yeast extract, 0.30% glucose, $p_H$ 7.2. The culture charges are incubated for 48 hours at 30° C. in the shaking machine, then diluted with 0.1% Tween 80 (polyoxyethylene sorbitane monooleate) and 0.1% cholesterol and after a further 4 hours $10^{-3}$ M α,α'-dipyridyl added. At the point of time of the inhibitor addition the $p_H$ value is adjusted to 8.0. The cultures are harvested after 62 hours and the content of BNC determined by customary thin layer chromatographic methods.

D. Wild strains which correspond to the definition given by the invention

The most effective of the tested strains were deposited with the American Type Culture Collection, Rockville, Md., U.S.A. or with the German Collection of Microorganisms, Grisebachstr. 8, 3400 Göttingen, Germany.

| Internal name | Deposition number | Group factor a | % BNC yield | Selection factor p | Taxonomy |
|---|---|---|---|---|---|
| SC-17 | DSM 1418 | 2.375 | 13 | 1.3 | Bacteria spec. (the exact identification follows in time) |
| SC-89 | DSM 1419 | 1.060 | 28 | 2.8 | Bacteria spec. (the exact identification follows in time) |
| SC-104 | ATCC 31455 | 1.320 | 19 | 1.9 | Bacteria spec. (the exact identification follows in time) |
| SC-138 | DSM 1423 | 2.940 | 29 | 2.9 | Bacteria spec. (the exact identification follows in time) |
| SC-309 | ATCC 31458 | 1.140 | 30 | 3.0 | Bacteria spec. |

-continued

| Internal name | Deposition number | Group factor a | % BNC yield | Selection factor p | Taxonomy |
|---|---|---|---|---|---|
| SC-335 | DSM 1424 | 1.220 | 21 | 2.1 | Bacteria spec. (the exact identification follows in time) |
| SC-338 | DSM 1425 | 2.600 | 34 | 3.4 | Bacteria spec. (the exact identification follows in time) |
| SC-353 | DSM 1426 | 1.660 | 34 | 3.4 | Bacteria spec. (the exact identification follows in time) |
| SC-358 | DSM 1427 | 1.800 | 35 | 3.5 | Bacteria spec. (the exact identification follows in time) |
| SC-372 | DSM 1428 | 1.360 | 38 | 3.8 | Bacteria spec. (the exact identification follows in time) |
| SC-392 | DSM 1429 | 1.220 | 29 | 2.9 | Bacteria spec. (the exact identification follows in time) |
| SC-403 | DSM 1430 | 1.040 | 32 | 3.2 | Bacteria spec. (the exact identification follows in time) |
| SC-407 | DSM 1431 | 1.560 | 27 | 2.7 | Bacteria spec. (the exact identification follows in time) |
| SC-420 | DSM 1432 | 1.280 | 25 | 2.5 | Bacteria spec. (the exact identification follows in time) |

EXAMPLE 2

A. Mutation

1. Mutation treatment with chemical media

The strain SC-309 is first propagated in the following nutrient solution (nutrient solution A): 0.8%, peptone, 0.9% yeast extract, 0.3% glucose, 0.06% Tween 80 (polyoxyethylene sorbitane monooleate), 0.06% sitosterol, $p_H$ 7.2. After attaining the logarithmic growth phase the culture solution is treated for 1.5 hours with the mutagenous agent 1-methyl-3-nitro-1-nitrosoguanidine in a concentration of 1 mg per ml culture broth. Subsequently the cells are centrifuged out, the mutagenous binding again removed by washing with physiologically sterile sodium chloride solution and the cells resuspended in fresh nutrient solution A and incubated.

2. Mutation treatment by means of ultra-violet radiation

The mutation treatment by ultra-violet radiation is effected with the same cell material as given under A 1. After attaining a logarithmic growth phase the cells of strain SC 309 are centrifuged off under sterile conditions, twice washed with sterile 0.1 m phosphate buffer ($p_H$ 6.5), resuspended in the same buffer and adjusted to a cell density of $10^8$ cells/ml under a microscope. 8 ml of this cell suspension is transferred to a petri dish and radiated for 90 seconds under the ultra violet lamp (distance 30 cm, UV radiation lamp of E. Schütt Jun., Göttingen). The cell suspension so treated is subsequently resuspended in fresh nutrient solution A and incubated.

B. Selection and isolation of desired defect mutants

1. Penicillin and "replica-plating" method

Culture treated as under A is incubated for about 72 seconds at 30° C. in the shaking machine until it attains a cell titre of $>10^9$ per ml of culture solution. 0.1 ml of this cell suspension is transferred into 10 ml of the following nutrient solution (nutrient solution B): 0.05% $NaH_2PO_4$, 0.20% $K_2HPO_4$, 0.05% $MgSO_4.7H_2O$, 0.02% $CaCl_2.2H_2O$, 0.005% $MnSO_4.4H_2O$, 0.005% $(Fe)_2SO_4.7H_2O$, 0.10% $(NH_4)SO_4$, 0.0001% biotine, 0.10% Tween 80 and 0.10% BNC. After shaking for 18 hours at 30° C. diluted with fresh, preheated nutrient solution of the same composition to about $10^6$ cells per ml, 1000 IU penicillin G are added and incubation for a further 7 hours is carried out. The antibioticum is then removed by centrifuging of the cells with washing with sterile, physiologic sodium chloride solution and the cells further incubated for 3 days in the above-mentioned medium with 0.2% sitosterol instead of BNC. The penicillin treatment is repeated once more and the cell suspension finally plated out on the same nutrient medium A plus 1.6% agar. After the propagation of the cells to visible colonies, the cells are transfered with the aid of the "replica stamp technique" on nutrient medium B plus 1.6% agar and those colonies are selected and used as strain cultures which are not able to continue to grow, or scarecly able, on this medium.

2. $p^{32}$ separation method and "replica stamp" technique

The culture treated as under A 1 is incubated for about 48 hours at 30° C. in the shaking machine until the cell titre of $>10^9$ is attained.

The growing culture is harvested by centrifuging and twice washed with physiological cooking salt solution. The cells are floated in a phosphate-free nutrient solution of the following compositions: 0.1% bisnorcholenone acid, 0.2% BRIJ 35, 0.2% ammonium sulfate, 0.8% NaCl, main water $p_H$ 7.0. It is shaken for 24 hours at 30° C., in which time the inoculated cell count of $10^8$ cells per ml is doubled. 1 m C $NaH_2=PO_4$ of specific activity of 200 m C/mMol is added to a sample of 20 ml. It is shaken for a further 24 hours at 30° C., then the culture is centrifuged off, three times washed with physiological cooking salt solution, absorbed in 20 ml of a 10% glycerol solution and frozen in 10 small tubes to 2 ml.

After storage for a variable length of time the frozen cultures are thawed out and plated on a glucose-peptone-yeast extract nutrient agar. The cell count of the still living bacteria after 3 weeks' storage declined to about 99.9%. The cells still living from this sample were, after growing into colonies from the full nutrient medium on agar with bisnorcholenone acid as a source of carbon were stamped off and those colonies selected which were not able to grow, or scarcely able, on the latter medium.

C. Choice of the most active plant defective mutants

After the separation and solution procedures under B 1 or B 2 about 90 strains were isolated.

In order to choose the most active BNC accumulating mutants all the strains were again tested in submersion culture. The cultivation was effected in reagency glasses each with 2 ml nutrient solution A. After 20 hours at 30° C. on the "Roler tube" 0.1% Tween 80 and 0.1% β-sitosterol were added and after a further 96 hours the transformation product was analysed by extraction and thin layer chromatography. It was thereby shown from the mutants which have been isolated by the penicillin method, that the strain SC-309-179 (ATCC 31459) with a BNC rate of formation of 30%, and from mutants which had been isolated according to the P$^{32}$ method, the strain SC-309-189 ( ATCC 31460) with a rate of 35%, were the most active strains.

EXAMPLE 3

A. BNC yield of the most active mutant strain

1. BNC yield of the strain SC-309-179

The strain SC-309-179 was cultured in 500 ml Erlenmeyer flask with nutrient solution of the following composition: 0.8% peptone, 0.9% yeast extract, 0.3% glucose, 0.06% Tween 80 (polyoxyethylene sorbitane mono-oleate), 0.06% β-sitosterol, p$_H$ 7.2. The culture was shaken in the shaking machine (shaking frequency 150 rpm) at 30° C. for 62 hours, then 0.1% BRIJ 35 (polyoxyethylene monolauryl ether) and 0.1% β-sitosterol were added and incubated for a further 120 hours. After termination of the cultures, samples were taken and these extracted and analysed by thin layer chromotography. Referred to the quantity of substrate put in 35% 3-oxo-pregna-1,4-diene-20-carboxyl acid and 4% 3-oxy-pregna-4-ene-20-carboxyl acid and small amounts of androst-1,4-diene-3,17-dione were formed.

2. BNC yield of strain SC-309-189

Under the same conditions as above-mentioned the strain SC-309-189 formed the following products: 42% 3-oxo-pregna-1,4-diene-20-carboxyl acid, 9% 3-oxo-pregna-4-ene-20-carboxyl acid and traces of AD and ADD.

We claim:

1. A process for the production of biologically pure microorganism defective mutants which are capable of producing 17-C-steroid-alpha-propionic acid compounds including 3-oxo-pregna-4-ene-20 carboxylic acid and 3-oxo-1,4-diene-20-carboxylic acid and mixtures thereof from 17-C-side chain steroid substrates by selective side chain degradation under aerobic conditions without substantial steroid ring degradation in the absence of ring degradation inhibitors, where the biologically pure microorganism defective mutants are obtained from a population of mutants containing undesired accompanying mutant strains wherein
    (a) a microorganism wild strain which is capable of growing on sterol compounds as a sole source of carbon is isolated and cultivated,
    (b) the wild strain is treated by a known mutation treatment, to give the mutant population,
    (c) the mutant population obtained from (b) is cultivated on separation medium on which the mutants capable of degrading the sterol compounds only to the C-17-steroid-alpha-propionic acid do not substantially grow, and
    (d) the mutant micrioorganisms capable of growing in (c) are killed off due to their growth or through the use of antibiotics or radioactive media thereby giving the biologically pure defective mutant strain and,
    (e) the biologically pure mutant strains that do not substantially grow are isolated and preserved.

2. A process according to claim 1 wherein the sterol compound contains a side chain in the 17-C position containing from 8 to 10 carbon atoms of saturated or unsaturated nature which yield the 17-C-steroid-alpha-propionic acid compound in the yield at least of 5 percent by weight of the starting sterol compound.

3. A process according to claim 1 wherein at step (a) the wild strain is isolated and cultivated on sterol compounds containing a side chain in the 17-C position having 8 to 10 carbon atoms and the resulting selective degradation of the side chain is according to the formula $$I = a \cdot 10^p$$

wherein a is the growth factor and p is the selectivity factor of the wild strain growth and the selectivity index I has at least the value of 1.

4. A process according to claim 3 wherein in the wild strains are isolated and cultivated such that the growth factor a is at least 0.2.

5. A process according to claim 3 wherein p has a value of at least 0.5.

6. A process according to claim 5 wherein the mutation treatment of the wild strains according to (b) is carried out under conditions of concentration and reaction time of the mutagenic agent such that the starting population of microorganisms is inactivated to the extent of from 10 to 99.999 percent.

7. A process according to claim 1 wherein the wild strain microorganism is selected from the group consisting of ATCC 31455, ATCC 31458, DSM 1418, DSM 1419, DSM 1423, DSM 1424, DSM 1425, DSM 1426, DSM 1427, DSM 1428, DSM 1429, DSM 1430, DSM 1431, and DSM 1432.

8. A process according to claim 3 for the production of 17-C-steroid-alpha-propionic acid compounds by microbial side chain degradation on a 17-C-side chain steroid substrate wherein
    (a) microorganism defective mutants which function in the absence of a steroid ring degradation inhibitor are cultivated on a fermentation broth in an aqueous nutrient medium under aerobic conditions in the presence of a steroid substrate thereby forming the 17-C-steroid-alpha-propionic acid compound and
    (b) the 17-C-steroid-alpha-propionic acid compounds so formed are isolated.

9. A process according to claim 8 wherein the defective mutants which are used are cultivated on a member selected from the group consisting of cholesterol and sitosterol and mixtures thereof under conditions which yield at least 15 percent of a member selected from the group consisting of 3-oxo-pregna-4-ene-20-carboxylic acid and 3-oxo-1,4-diene-20-carboxylic acid and mixtures thereof.

10. A process according to claim 8 wherein the defective mutant is selected from the group consisting of ATCC 31456, ATCC 31457, ATCC 31459, and ATCC 31460.

11. A process according to claim 8 wherein the wild strain which is the source of the defective mutant is selected from the group consisting of ATCC 31455, ATCC 31458, DSM 1418, DSM 1419, DSM 1423, DSM 1424, DSM 1425, DSM 1426, DSM 1427, DSM 1428, DSM 1429, DSM 1430, DSM 1431, and DSM 1432.

12. A biologically pure culture of defective mutant strains selected from the group consisting of ATCC 31456, ATCC 31457, ATCC 31459 and ATCC 31460.

* * * * *